(12) United States Patent
Khafizova

(10) Patent No.: US 8,928,606 B1
(45) Date of Patent: Jan. 6, 2015

(54) SYSTEM AND METHOD FOR ANALYSING DATA RECORDS UTILIZING A TOUCH SCREEN INTERFACE

(75) Inventor: Margarita Khafizova, Plano, TX (US)

(73) Assignee: Open Invention Network, LLC, Durham, NC (US)

( * ) Notice: Subject to any disclaimer, the term of this patent is extended or adjusted under 35 U.S.C. 154(b) by 0 days.

(21) Appl. No.: 13/454,495

(22) Filed: Apr. 24, 2012

Related U.S. Application Data

(63) Continuation of application No. 13/033,798, filed on Feb. 24, 2011.

(60) Provisional application No. 61/317,741, filed on Mar. 26, 2010.

(51) Int. Cl.
*G06F 3/041* (2006.01)

(52) U.S. Cl.
USPC ............... 345/173; 345/418; 705/3; 715/702; 715/835

(58) Field of Classification Search
CPC ... G06Q 50/24; G06Q 10/10; G06Q 10/0833; G06F 19/322; G06F 19/3418; G06F 3/0488; G06F 19/324; G06F 19/325; G06F 19/3487; G06F 19/363; G06F 19/3431; G06F 19/345; G06F 17/30713; G06F 19/30; G06F 19/323; G06T 11/206

USPC .............. 345/173, 419, 418; 715/835
See application file for complete search history.

(56) References Cited

U.S. PATENT DOCUMENTS

| | | | |
|---|---|---|---|
| 7,343,565 B2 | 3/2008 | Ying et al. | |
| 7,499,046 B1 * | 3/2009 | Wright et al. | 345/418 |
| 7,519,223 B2 | 4/2009 | Dehlin et al. | |
| 8,407,282 B2 * | 3/2013 | Cogan | 709/203 |
| 2006/0265249 A1 * | 11/2006 | Follis et al. | 705/3 |
| 2007/0229471 A1 * | 10/2007 | Kim et al. | 345/173 |
| 2008/0244453 A1 * | 10/2008 | Cafer | 715/835 |
| 2009/0262894 A1 | 10/2009 | Shukla et al. | |
| 2010/0058182 A1 * | 3/2010 | Jung | 715/702 |
| 2010/0162153 A1 * | 6/2010 | Lau | 715/769 |
| 2011/0125528 A1 * | 5/2011 | Padate et al. | 705/3 |
| 2013/0246097 A1 * | 9/2013 | Kenney et al. | 705/3 |

* cited by examiner

*Primary Examiner* — Amare Mengistu
*Assistant Examiner* — Gloryvid Figueroa-Gibson
(74) *Attorney, Agent, or Firm* — Haynes and Boone, LLP

(57) ABSTRACT

Certain aspects of the present disclosure relate to a technique for analyzing data records using a touch screen interface. A touch event is received from the touch screen interface. In response to receiving the touch event, at least one data record is selected from a plurality of data records in a time chart, the time chart including at least one time line relating to at least one data object, the plurality of data records being plotted on the at least one time line based on a time parameter of each of the plurality of data records. Information relating to the selected at least one data record is processed based on the time parameter.

21 Claims, 13 Drawing Sheets

```
<?xml version="1.0" encoding="ISO-8859-1" ?>
<MEDICALRECORD>
 <CASE>
        <REC>REC4384023</REC>
        <PATIENTID>PID123456789</PATIENTID>
        <DATE>04.07.1985</DATE>
        <FIRSTNAME>John</FIRSTNAME>
        <MIDDLENAME>Smith</MIDDLENAME>
        <LASTNAME>Smith</LASTNAME>
        <DOB>01.10.1920</DOB>
        <ADDRESS>1 MAIN STREET, APT 1, SMALLTOWN, BIGSTATE</ADDRESS>
        <COUNTRY>USA</COUNTRY>
        <ZIP>12345</ZIP>
        <SYMPTOMS>COUGH, HEADACHE</SYMPTOMS>
        <VITALSIGNS>
           <TEMP> 102F </TEMP>
           <BP> 120/80 </BP>
           <WEIGHT> 102F </WEIGHT>
           <HEIGHT> 5-10 </HEIGHT>
        </VITALSIGNS>
        <DIAGNOSIS>BRONCHITIS</DIAGNOSIS>
        <OBSERVATION>MODERATE BRONCHITIS SYMPTOMS</OBSERVATION>
        <RECOMMENDATIONS>REST</RECOMMENDATIONS>
        <PRESCRIBEDMEDICATION></       PRESCRIBEDMEDICATION>
        <LABEXAMREFERENCE>LAB12345678</LABEXAMREFERENCE>
        <RELATEDCASE>REC4683920</RELATEDCASE>
 </CASE>
</MEDICALRECORD>
```

FIG. 6B

```xml
<?xml version="1.0" encoding="ISO-8859-1" ?>
<PATIENTPROFILE>
    <PATIENTID>PID123456789</PATIENTID>
        <FIRSTNAME>John</FIRSTNAME>
        <MIDDLENAME>Joe</MIDDLENAME>
        <LASTNAME>Smith</LASTNAME>
        <DOB>01.10.1920</DOB>
        <ADDRESS>1 MAIN STREET, APT 1, SMALLTOWN, BIGSTATE</ADDRESS>
        <COUNTRY>USA</COUNTRY>
        <ZIP>12345</ZIP>
        <FATHER> PID123456700</FATHER>
        <MOTHER> PID123456701</MOTHER>
        <NCHILDREN> 1 </ NCHILDREN >
        <CHILD> PID123456702</CHILD>
        <NSIBLINGS> 0 </NSIBLINGS >
</ PATIENTPROFILE >
```

FIG. 6C

SYSTEM AND METHOD FOR ANALYSING DATA RECORDS UTILIZING A TOUCH SCREEN INTERFACE

CROSS REFERENCE TO RELATED APPLICATIONS

This application is a continuation of and claims priority from U.S. application Ser. No. 13/033,798, filed on Feb. 24, 2011, entitled "SYSTEM AND METHOD FOR ANALYSING DATA RECORDS UTILIZING A TOUCH SCREEN INTERFACE", which in turn claims priority from U.S. Provisional application Ser. No. 61/317,741 entitled 'SYSTEM AND METHOD FOR ANALYSING DATA RECORDS UTILIZING A TOUCH SCREEN INTERFACE' as filed on Mar. 26, 2010. The above applications are incorporated herein by reference.

TECHNICAL FIELD OF THE INVENTION

The present disclosure relates generally to touch sensitive devices and, more specifically, to a method, apparatus and computer-readable medium for analyzing data records on a time chart using a touch screen interface.

BACKGROUND OF THE INVENTION

User interface (UI) is often one of the most important parts of a computer program because it determines how easily a user can communicate with the program. A powerful program with a poorly designed UI has little value. Text-based and graphical user interfaces (GUIs) that use windows, icons, and pop-up menus have become standard on personal computers. Text-based UIs as well as GUIs typically use an input device, such as a keyboard, mouse or stylus, to provide user input and control the movement of a cursor or pointer on a display screen.

Touch-sensitive surfaces are rapidly becoming more common in computing devices. A natural input device for computing devices with touch-sensitive surfaces is a user's finger. They are very convenient as they allow a user to make natural gestures familiar to the user in other contexts, such as by entering handwriting using a stylus. Many of these devices also allow input to be provided by a user's fingertip. The term touch-sensitive surface or device will be used herein to refer to such surfaces or devices that are configured to detect the touch of any type of "stylus" such as a stylus, stylus type device or a user's finger, fingers, hand or hands.

As portable electronic devices become more compact, and the number of functions performed by a given device increase, it has become a significant challenge to design a user interface that allows users to easily interact with various devices including multifunction devices. This challenge is particularly significant for handheld portable devices, which have much smaller screens than desktop or laptop computers. This situation is unfortunate because the user interface is the gateway through which users receive not only content but also respond to user actions or behaviors, including user attempts to access a device's features, tools, and functions. Some portable communication devices (e.g., PDAs, mobile telephones, sometimes called mobile phones, cell phones, cellular telephones, smart phones, and the like) have resorted to adding more pushbuttons, increasing the density of push buttons, overloading the functions of pushbuttons, or using complex menu systems to allow a user to access, store and manipulate data. These conventional user interfaces often result in complicated key sequences and menu hierarchies that must be memorized and accessed by the user.

Many conventional user interfaces, such as those that include physical pushbuttons, are also inflexible. This may prevent a user interface from being configured and/or adapted by either an application running on the portable device or by users. When coupled with the time consuming requirement to memorize multiple key sequences and menu hierarchies, and the difficulty in activating a desired pushbutton, such inflexibility is frustrating to most users.

To avoid problems associated with pushbuttons and complex menu systems, portable electronic devices may use touch screen displays with simple and intuitive interfaces. Each set of applications may require a specific set of touch commands, however in many cases commands are obvious and require very little or no learning time. Conventional interfaces make some sophisticated software tools unusable by many people not skilled in using high-tech gadgets. Accordingly, there is a need for touch screen display electronic devices with more transparent and intuitive user interfaces. Such interfaces increase the effectiveness, efficiency and user satisfaction with portable multifunction devices. The need to elaborate methods of touch screen device user's gesture recognition and flexible touch commands has been recognized in both industry and academia. Numerous inventions have been reported in that area. For example, in U.S. Pat. No. 7,519,223 "Recognizing gestures and using gestures for interacting with software applications" by Dehlin et al, an interactive display table is described that senses and infers natural hand or finger positions, or movement of an object, to detect gestures. Specific gestures are used to execute applications, carryout functions in an application, create a virtual object, or do other interactions, each of which is associated with a different gesture.

Unfortunately, there are few if any systems applying touch screen technology to important tasks related to processing data records. One important set of applications that could greatly benefit from a new and intuitive interface based on touch screen display technology is analysis of data records and/or files with similar content. For example, medical records which are being currently transferred from paper to electronic format(s). Advancements in online and document tracking technologies (e.g., XML, SGML, etc.) make it possible to standardize medical records. E.g., U.S. Pat. No. 7,624,027 "Method and system for automated medical records processing" by Stern et al provides a means for reducing the complexity of collecting patient information and helps to generate the appropriate number and type of medical codes for a specific type of medical process or practice when processed. One embodiment also includes processing applications that allow easy and automated collection, processing, displaying and recording of medical codes (e.g., diagnosis codes, billing codes, insurance codes, etc.), medical records and other medical data. The medical codes, records and data including patient encounter information are displayed in real-time on electronic templates prior to, during or immediately after a patient encounter.

In the United States, the development of standards for Electronic Medical Records (EMR) interoperability is at the forefront of the national health care agenda. EMRs are an important factor in interoperability and sharing data between practicing physicians, pharmacies and hospitals. Many physicians currently have computerized practice management systems that can be used in conjunction with health information exchange (HIE), allowing for first steps in sharing patient information (lab results, public health reporting) which are necessary for timely, patient-centered and portable care. In the United States, approximately one-quarter of office-based physicians reported fully or partially using EMR systems in 2005. A complete EMR system has four basic functions: computerized orders for prescriptions, computerized orders for tests, reporting of test results, and physician notes. During examination of a patient's medical history it is often valuable to examine and compare medical records of relatives because such records may provide additional information related to the patient's medical issue. Therefore, a system, method and computer readable medium facilitating such examination and comparison is needed. With the growing popularity of touch screen technology, it is necessary to deploy such features on computing devices with touch screen interfaces. Ease of use and intuitive interface of touch screen computing devices will make such features popular in the medical field.

What is also needed is an application that can be utilized with a device including a touch screen or display (such as a mobile device or desktop monitor) that allows the user to align data, displayed on a touch screen, according to an identifier or tag associated with one or more data units. The tag could be a time tag, for example, a timestamp relating data units to events that occurred sometime in the past or will occur in the future. Alternatively, the tag could be the distance from a reference point, and it could be associated with data units describing real estate items such as houses, office buildings, data centers, etc. Applications taking advantage of such commands will be described in embodiments below. Some of the applications can be specialized (e.g., in the medical field) and suitable for touch screen devices larger than the ones used in mobile handset devices. In the embodiments below, the benefits of relevant simple and intuitive touch screen commands will be disclosed.

The present invention can be used with various applications. These applications include but are not limited to the analysis of medical reports, displaying numerous historic events, for example, in museums or in schools during history lessons. These applications are given only as examples, and it should be noted that the invented touch screen commands could also be used in other applications such as map applications. Any person skilled in the art will recognize that this invention can be used in many other applications.

SUMMARY OF THE INVENTION

Certain aspects of the present disclosure provide a method for analyzing data records using a touch screen interface. The method generally includes receiving a touch event from the touch screen interface, in response to receiving the touch event, selecting at least one data record from a plurality of data records in a time chart, the time chart including at least one time line relating to at least one data object, the plurality of data records being plotted on the at least one time line based on a time parameter of each of the plurality of data records and processing an information relating to the selected at least one data record based on the time parameter.

Certain aspects of the present disclosure provide an apparatus for analyzing data records using a touch screen interface. The apparatus generally includes at least one processor and a memory coupled to the at least one processor. The processor is generally configured to receive a touch event from the touch screen interface, in response to receiving the touch event, select at least one data record from a plurality of data records in a time chart, the time chart including at least one time line relating to at least one data object, the plurality of data records being plotted on the at least one time line based on a time parameter of each of the plurality of data records and process an information relating to the selected at least one data record based on the time parameter.

Certain aspects of the present disclosure provide a computer-program product for analyzing data records using a touch screen interface, the computer-program product generally including a computer-readable medium comprising instructions for receiving a touch event from the touch screen interface, in response to receiving the touch event, selecting at least one data record from a plurality of data records in a time chart, the time chart including at least one time line relating to at least one data object, the plurality of data records being plotted on the at least one time line based on a time parameter of each of the plurality of data records and processing an information relating to the selected at least one data record based on the time parameter.

BRIEF DESCRIPTION OF THE DRAWINGS

FIG. 6B illustrates a sample medical record in XML format according to an embodiment of the present application.

FIG. 6C illustrates a sample patient's profile in XML format according to an embodiment of the present application.

Figure 1:
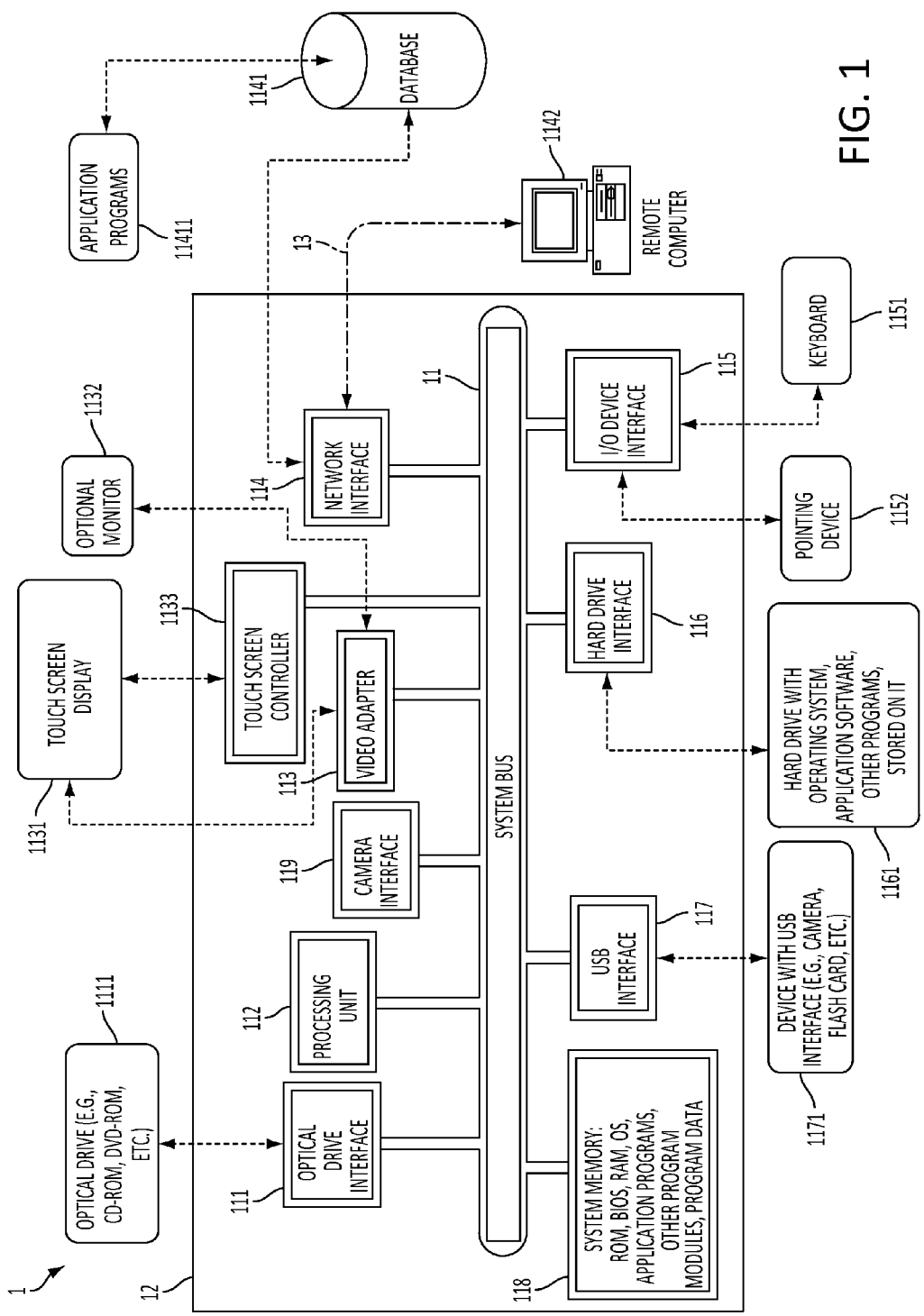
FIG. 1 illustrates a functional block diagram of a generally conventional computing device or personal computer that is suitable for analysis of data records in connection with an interactive display table, in accord with one embodiment of the present application.

The foregoing summary, as well as the following detailed description of certain embodiments of the present invention, will be better understood when read in conjunction with the drawings. The drawings illustrate functional blocks of various embodiments. The functional blocks are not necessarily indicative of the division between hardware circuitry. Thus, for example, one or more of the functional blocks (e.g., processors or memories) may be implemented in a single piece of hardware (e.g., a general purpose signal processor or a block or random access memory, hard disk, or the like). Similarly, the programs may be stand alone programs, may be incorporated as subroutines in an operating system, may be functions in an installed imaging software package, and the like. It should be understood that the various embodiments are not limited to the arrangements and instrumentality shown in the drawings.

DETAILED DESCRIPTION OF ILLUSTRATIVE EMBODIMENTS

Aspects of the present invention can be used in connection with a computing device including a touch screen. With reference to FIG. 1, an exemplary system 1 suitable for implementing various portions of the present invention is shown. The system includes a general purpose computing device in the form of a conventional computer (PC) 12, provided with a processing unit 112, a system memory 118, and a system bus 11. The system bus couples various system components including the system memory to processing unit 112 and may be any of several types of bus structures, including a memory bus or memory controller, a peripheral bus, and a local bus using any of a variety of bus architectures. The system memory includes read only memory (ROM) and random access memory (RAM). A basic input/output system (BIOS), containing the basic routines that help to transfer information between elements within the PC 12, such as during start up, is stored in ROM. The PC 12 further includes a hard disk drive 1161 for reading from and writing to a hard disk (not shown), an optical disk drive 1111 for reading from or writing to a removable optical disk, such as a compact disk-read only memory (CD-ROM) or other optical media. Hard disk drive 1161 and optical disk drive 1111 are connected to system bus 11 by a hard disk drive interface 116 and an optical disk drive interface 111, respectively. The drives and their associated computer readable media provide nonvolatile storage of computer readable machine instructions, data structures, program modules, and other data for PC 12. Although the exemplary environment described herein employs a hard disk and removable optical disk, it will be appreciated by those skilled in the art that other types of computer readable media, which can store data and machine instructions that are accessible by a computer, such as magnetic disks, magnetic cassettes, flash memory cards, digital video disks (DVDs), Bernoulli cartridges, RAMs, ROMs, and the like, may also be used in the exemplary operating environment.

A number of program modules may be stored on the hard disk, optical disk, ROM, or RAM, including an operating system, one or more application programs, other program modules, and program data. A user may enter commands and information via the PC 12 and provide control input through input devices, such as a keyboard 1151 or a pointing device 1152. Pointing device 1152 may include a mouse, stylus, wireless remote control, or other pointer, but in connection with the present invention, such conventional pointing devices may be omitted, since the user can employ the touch sensitive interactive display for input and control. As used hereinafter, the term "mouse" is intended to encompass virtually any pointing device that is useful for controlling the position of a cursor on the screen. Other input devices (not shown) may include a microphone, joystick, haptic joystick, yoke, foot pedals, game pad, satellite dish, scanner, or the like. These and other input/output (I/O) devices are often connected to processing unit 112 through an I/O interface 115 that is coupled to the system bus 11. The term I/O interface is intended to encompass each interface specifically used for a serial port, a parallel port, a game port, a keyboard port, and/or a universal serial bus (USB).

Figure 2:
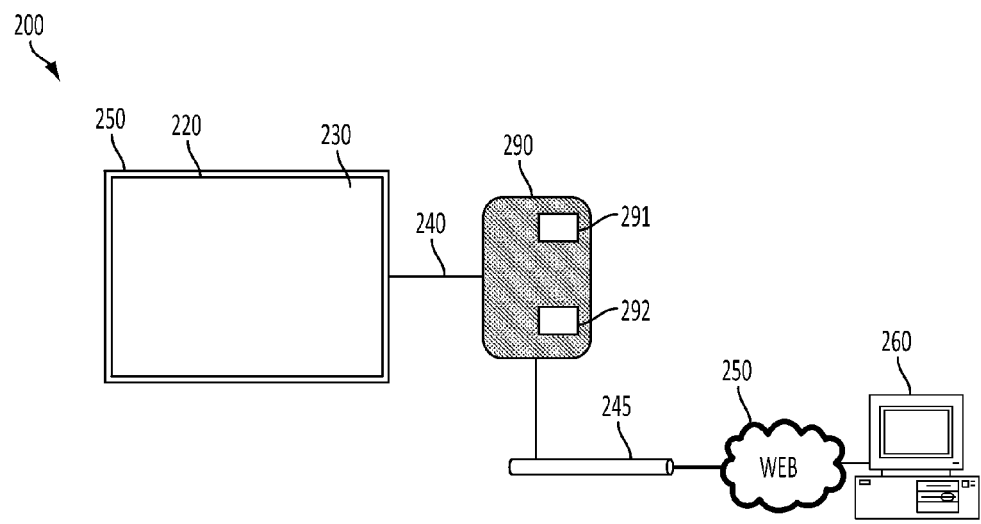
FIG. 2 illustrates a system with a touch screen capable of detecting touch events in accordance with one embodiment of the present application.

System bus 11 is also connected to a camera interface 119. The digital video camera may be instead coupled to an appropriate serial I/O port, such as to a USB port. Optionally, a monitor 1132 can be connected to system bus 11 via an appropriate interface, such as a video adapter 113; however, the touch screen display 1131 of the present invention can provide a much richer experience for the user and interact with the user for input of information and control of software applications and is therefore preferably coupled to the video adaptor. The touch screen display with a touch sensor 1131, communicatively coupled to the touch controller 1133. Touch sensor and controller can be combined in one block or they can be separate and communicatively coupled blocks as is illustrated in FIG. 1. It should be noted that the touch screen display, the touch screen sensor and controller can be enclosed into a single device as well. Various sensing technologies are applied in touch input systems currently in marketplace, including acoustic, resistive, capacitive and infrared. While any of these touch sensing technologies can be used in for illustration of present invention, the preferred embodiment of this invention assumes acoustic wave based touch sensing technology. FIG. 2 below illustrates touch sensing system with a touch screen in more detail. Please refer to the referenced application "Repetitive touch combining method" for more details on acoustic touch sensing technology.

User interface can be implemented through the optional monitor 1132 coupled with the touch sensor and controller 1133 though the video adapter 113 or directly via internet, wireless, or another connection. It will be appreciated that PCs are often coupled to other peripheral output devices (not shown), such as speakers (through a sound card or other audio interface—not shown) and printers.

The present invention may be practiced on a single machine, although PC 12 can also operate in a networked environment using logical connections to one or more remote computers, such as a remote computer 1142. Remote computer 1142 may be another PC, a server (which can be configured much like PC 12), a router, a network PC, a peer device, or a satellite or other common network node, and typically includes many or all of the elements described above in connection with PC 12. The logical connection 13 depicted in FIG. 1 can be a local area network (LAN) or a wide area network (WAN). Such networking environments are common in offices, enterprise wide computer networks, intranets, and the Internet.

When used in a LAN networking environment, PC 12 is connected to a LAN through a network interface or adapter 114. When used in a WAN networking environment, PC 12 typically includes a modem (not shown), or other means such as a cable modem, Digital Subscriber Line (DSL) interface, or an Integrated Service Digital Network (ISDN) interface for establishing communications over WAN, such as the Internet. The modem, which may be internal or external, is connected to the system bus 11 or coupled to the bus via I/O device interface 115, i.e., through a serial port. In a networked environment, program modules, or portions thereof, used by PC 12 may be stored in the remote memory storage device. It will be appreciated that the network connections shown are exemplary and other means of establishing a communications link between the computers may be used, such as wireless communication and wide band network links.

FIG. 2 illustrates a system 200 with a touch screen 220 capable of detecting touch events in accordance with an embodiment of the present invention. A touch sensor system with a single touch-screen device 250 is illustrated in FIG. 2. The touch-screen device 250, communicatively coupled to a controller 290 through link 240, includes a transparent touch sensor layer 230 covered by a touch-screen 220 made out of transparent material such as glass. The controller 290 further comprises at least one buffer 291 and at least one specialized microprocessor 292. The purpose of the microprocessor 292 is to process signals received from the touch screen display sensors. It should be noted that the buffer 291 and the microprocessor 292 can be combined with the existing buffer(s) and microprocessor(s) of controllers used in other systems.

A touch-screen system comprising the touch-screen device 250 and controller 290 may be used in conjunction with a controller user interface unit 260 coupled with the controller 290 via direct link, Internet/web 250, wireless, or another connection. It should be noted that controller 290 and controller interface units may be built in to the touch-screen device 250. Separate units 250, 290, and 260 are shown for illustrating a more general example.

The microprocessor 290 may output the combined information of detected touch events to another device such as a central or host computer 260 via lead 245. It should be understood that the coordinate information passed through the lead 245 is representative only. In addition, information may be output in many forms and formats by the computer 260, such as text or graphics on the display device 250, a different display device or monitor, a light, a bell, an initiation or termination of an action, and the like. Therefore, the information passed through the lead 245 may change based on the purpose of the touch sensor system 200. Optionally, the controller 290 may be located within a monitor or the display device 250, in a separate unit as illustrated, or within the computer 260.

One embodiment of the invention discloses a medical record system. Advancements in online and document tracking technologies (e.g., XML, SGML, etc.) make it possible to standardize medical records. In the United States, the development of standards for Electronic Medical Records (EMR) interoperability is at the forefront of the national health care agenda. EMRs are an important factor in interoperability and sharing data between physicians, pharmacies and hospitals. Many physicians currently have computerized practice management systems that can be used in conjunction with health information exchange (HIE), allowing for sharing of patient information (lab results, public health reporting) which are necessary for timely, patient-centered and portable care.

In the United States, approximately one-quarter of office-based physicians reported fully or partially using EMR systems in 2005. A complete EMR system has four basic functions: computerized orders for prescriptions, computerized orders for tests, reporting of test results, and physician notes. During examination of a patient's medical history it is often valuable to examine and compare medical records of relatives because such records may provide additional information related to the patient's medical issue. Therefore, a system, method and computer readable medium facilitating such examination and comparison is needed. With the growing popularity of touch screen technology, it is necessary to deploy such features on computing devices with touch screen interfaces. Ease of use and intuitive interface of touch screen computing devices will make such features popular in the medical field.

Figure 3A:
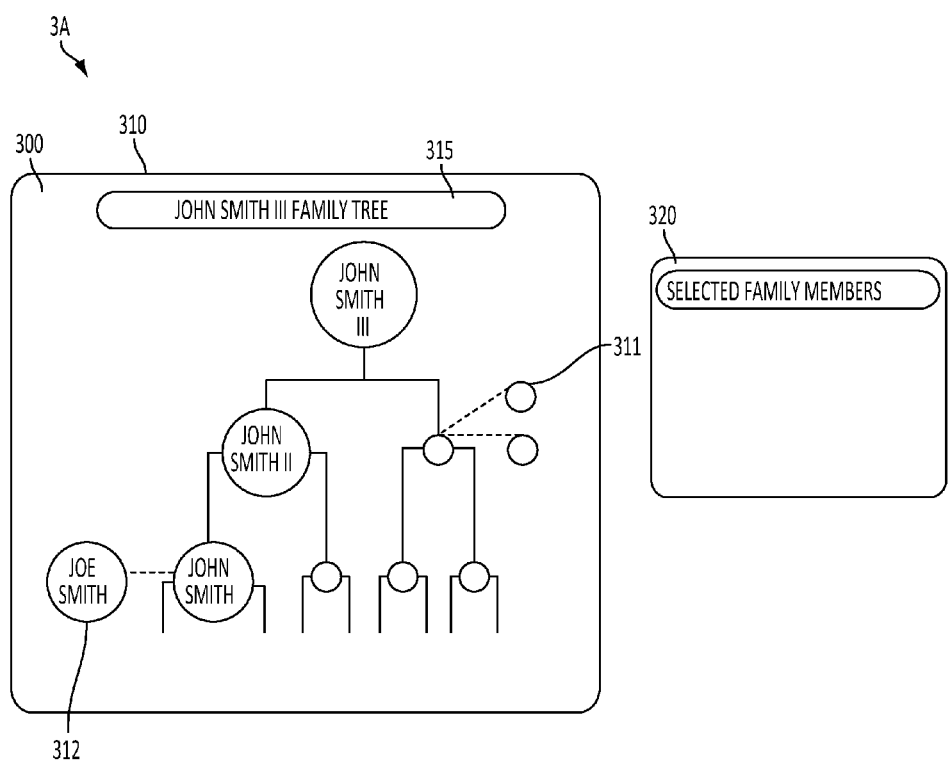
FIG. 3A illustrates selection of people in a family tree in accordance with one embodiment of the present application.
Figure 3B:
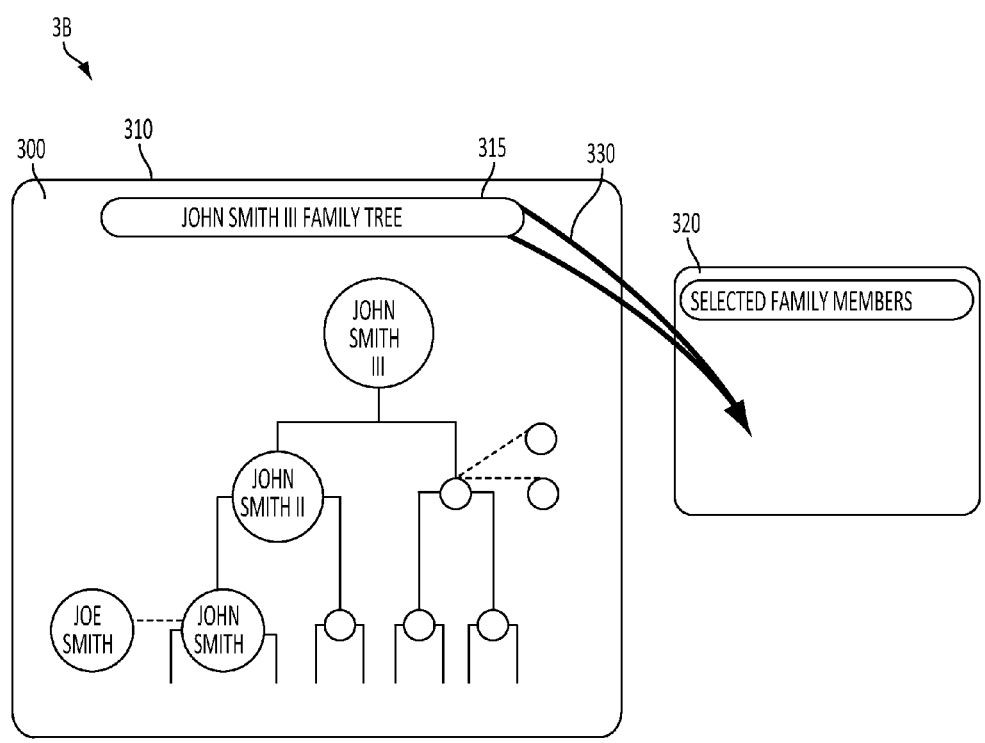
FIG. 3B illustrates a user moving people selected from the family tree into a corresponding window via a touch command in accordance with one embodiment of the present application.

In FIG. 3A and FIG. 3B two windows are shown for selecting a set of relatives of a patient whose medical history is being examined by the doctor. The invented system allows the doctor to open a window for selections of relatives of a patient. For the purpose of this illustration we assume that patient's name is John Smith III, and many medical records of his family members, electronic medical records of his father (John Smith II), paternal grandfather (John Smith I), and grandfather's brother (Joe Smith) are available. In the invented system the doctor enters the patient's name and touches a button such as "EXAMINE FAMILY TREE" (not shown) and the desired level of the tree (TREE_LEVEL). For the purpose of this example, we will assume that the desired tree level is three, i.e. TREE_LEVEL=3.

The system opens a window 310 of patient's family tree with the title 315 of the window (e.g., "John Smith III family tree" in this example) and window 320 of selected family members, which remains empty until the selection is completed. In one embodiment, the family tree is shown as a binary tree with a father on the left and mother to the right of each person in the tree. Siblings are connected with dotted lines. In this embodiment, nodes corresponding to male siblings are on the left of the node corresponding to the person whose siblings are considered, and nodes of female siblings are to the right. For example node 311 corresponds to sister of the mother of John Smith III; and node 312 corresponding to Joe Smith, brother of John Smith I, is on the left of the node corresponding to John Smith I. Nodes corresponding to siblings are connected by a dotted line. Initially the names of relatives are not shown in the tree. There is an option, however, to make all names visible, or to show fictitious names or other identifiers, if privacy issues are of concern. Details of the implementation of family tree construction will be described later (please see FIG. 3C and the related description).

By touching with his finger, via such screen 300, the nodes of desired relatives, a doctor selects family members whose records he wants to examine and to compare. Nodes corresponding to selected family members are highlighted as shown in FIG. 3A. Details of the implementation of family tree construction will be described later (please see FIG. 3D and the related description). Once all desired family members are selected, the doctor can simply touch inside the window 310 and move inside the window 320 as shown in FIG. 3B. Upon completion of this operation content of window 320 "Selected Family Members" is filled. The result of this example can be seen as window 5000 in FIG. 5. It contains a box with the name of the main patient (John Smith III) on top, and boxes with the names of selected relatives below. This window will be used later to combine selected patients with the group of medical disorders that the doctor wants to analyze.

Figure 3C:
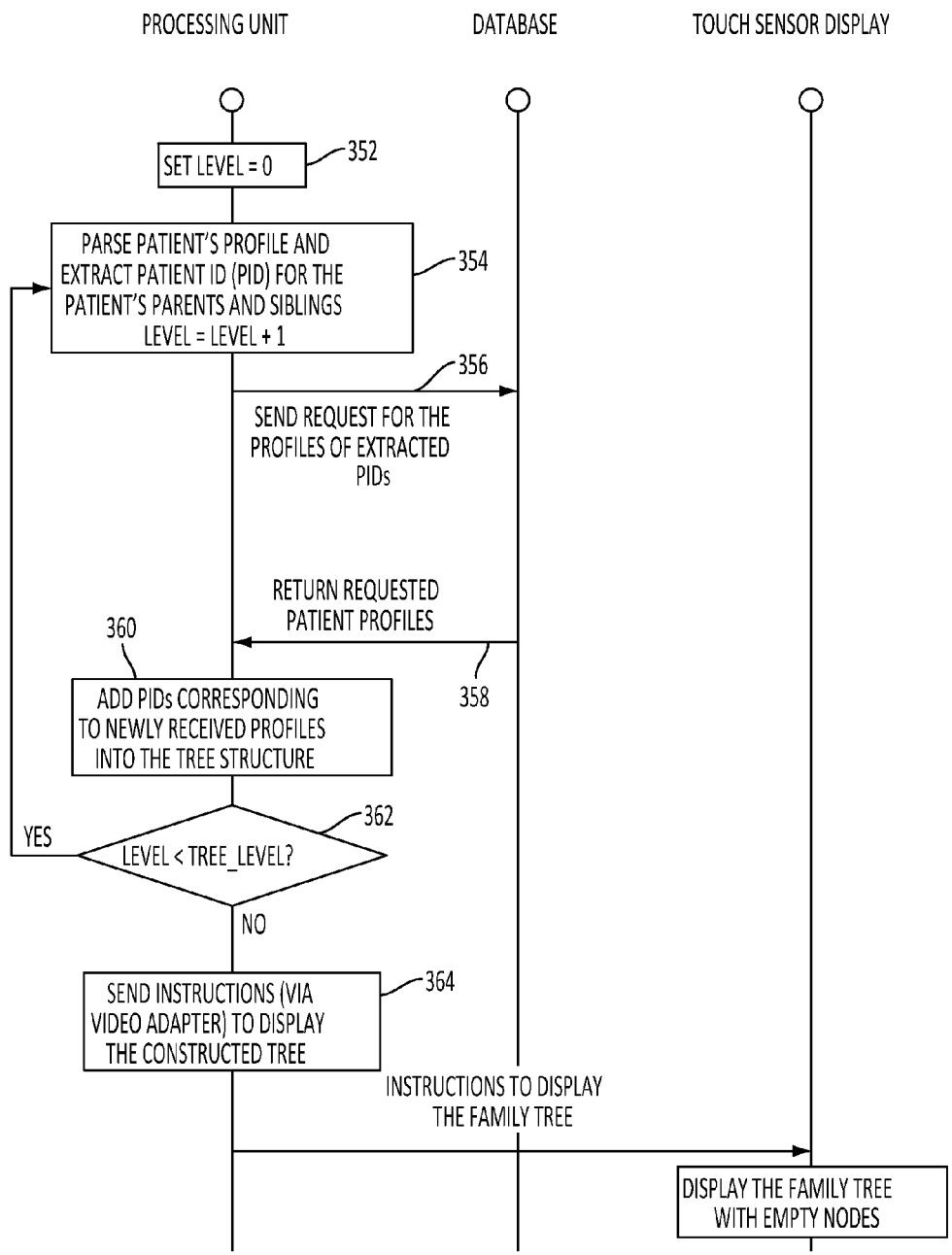
FIG. 3C illustrates a process of family tree construction according to one embodiment of the present application.

Details of how the family tree can be constructed are explained in this section and are illustrated in flow chart shown in FIG. 3C below. At 352, the tree level is set to zero. At 354, Processing unit 112 of the system shown in FIG. 1 will parse the patient's (John Smith III) profile (see FIG. 6B), and will extract PIDs of the patient's parents and siblings. For each of the extracted PIDs, the program running on the Processing Unit 112 of the system 1 in FIG. 1 will form a query for the profile of each parent and send it to the data base 1141 at 356. The patient profiles corresponding to the PIDs are returned to the processing unit at 358. At 360, the software running on the Processing unit 112 will form a tree structure and assign corresponding PID to each of the node. The tree level is checked at 362 and the process is be repeated for each of the PIDs up to the number=TREE_LEVEL (defined above). Re-call that in our example TREE_LEVEL=3. At 364, graphical commands are sent to the video adapter 113

(see FIG. 1) so that the tree is displayed on the touch screen display. These steps are illustrated in the flow chart shown in FIG. 3C.

Figure 3D:
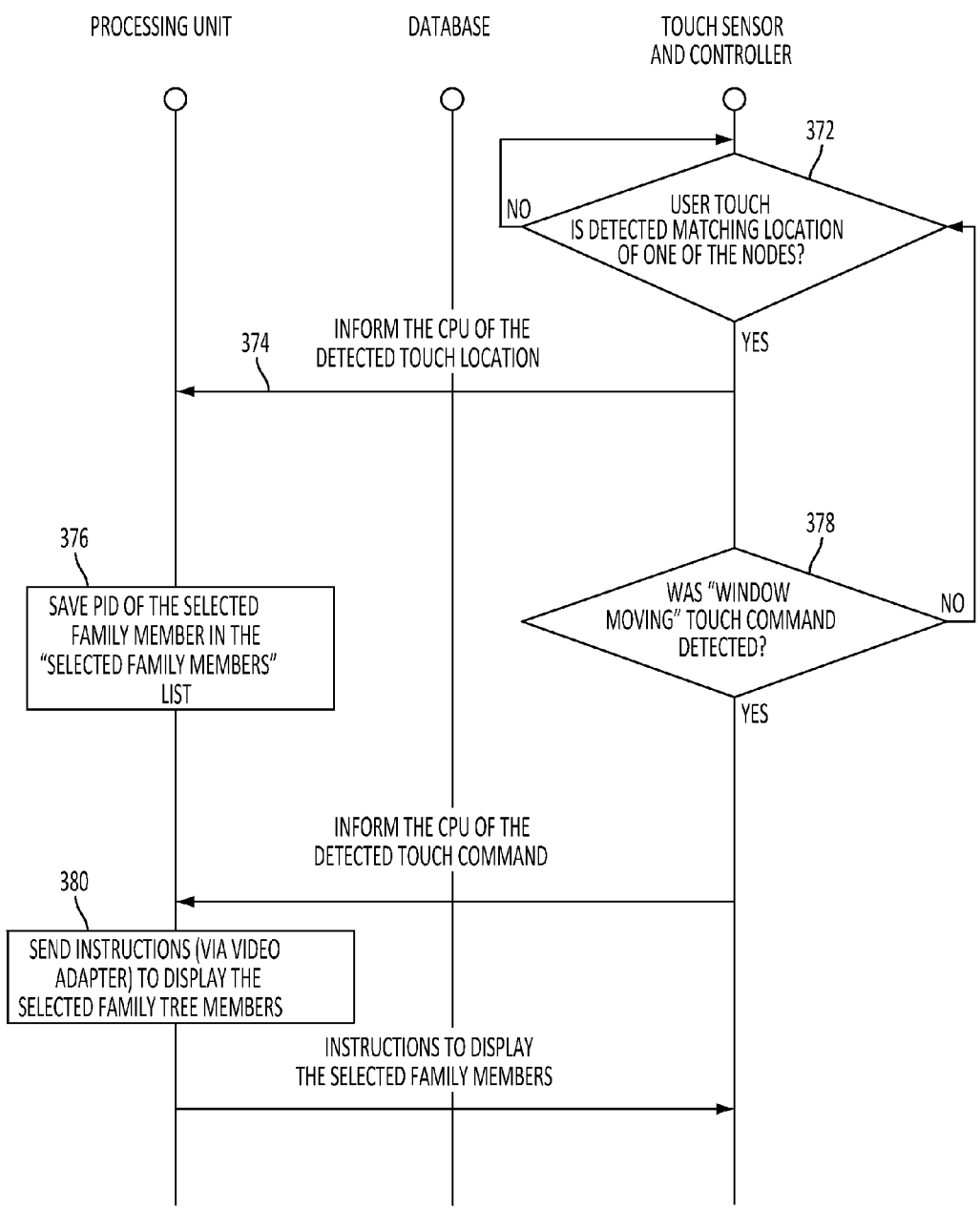
FIG. 3D illustrates a process of selecting family tree members according to one embodiment of the present application.

Details of how the desired family member selection shown in FIG. 3A can be implemented is described in this section and is illustrated in the flow chart shown in FIG. 3D. Once the family tree shown in window, touch sensor of the touch screen will detect finger touches at 372 and report them to the controller at 374. In FIG. 1 touch sensor and controller are shown as one unit 1133, but in other embodiments they can separate units. Please refer to "Repetitive touch combining method" invention disclosure for the detailed description of a possible implementation of (acoustic) touch detection technology. If the processing unit 112 (see FIG. 1) identifies location of the detected touch with a node on the family tree, at 376 the corresponding family member is put into the "selected family members" list and the corresponding node highlighting instructions are sent to the controller. The process is repeated until a different touch command is detected by the sensor and controller 1133 at 378. This is a touch command shown in FIG. 3B and described earlier. When that command occurs, the processing unit interprets this a completion of family member selection and sends instructions 380 to display selected family members as is seen in window 5000 of FIG. 5.

Figure 4:
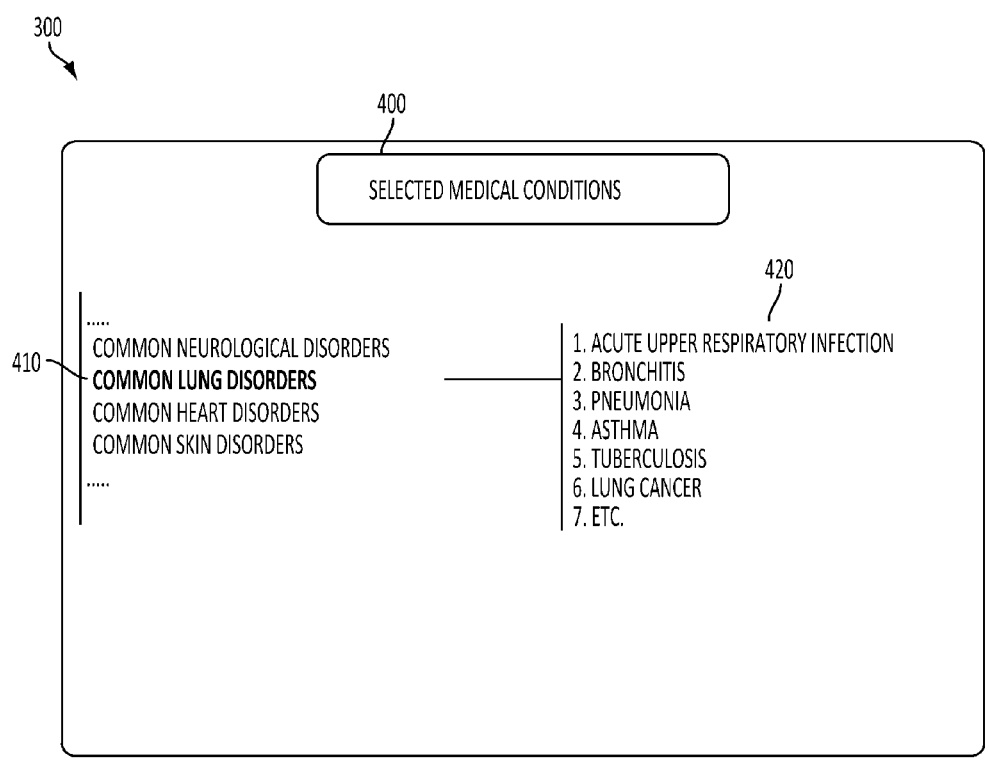
FIG. 4 illustrates a process of a user selecting a set of medical disorders that will be analyzed for those selected by a touch command according to one embodiment of the present application.

In FIG. 4 another window 400 is opened by the application which allows the doctor to specify medical records of what medical disorders the doctor wants to examine and compare. For example, if the doctor is concerned with the lung problems of John Smith III, he may select "Common Lung Medical disorders" by touching with his finger, via touch screen 300, the corresponding line in the list 410 of common medical disorders shown in FIG. 4. Immediately upon selection of this group, the touched line is highlighted (e.g., in blue color as shown), and the list 420 of the corresponding medical disorders from the selected group are shown on the right hand side.

The invented system allows a natural and intuitive way of invoking desired medical records related to selected persons. Once family members and a group of medical disorders are selected, the doctor can instruct the system to invoke for selected people all the medical records with diagnosis related to one or more of selected medical disorders. In the preferred embodiment, this is done by a simple touch command shown in FIG. 5. The user touches with his finger, via touch screen 300, the window of selected medical disorders 5200 and moves it into the window 5000 of selected family members. Auxiliary windows 5100 and 5300 are displayed by the system to assist the user with information shown in the main top windows. For example, window 5100 specifies the name of the main person, whose family members' records are being examined. This is useful in case the number of selected family members is large and can not be easily displayed in the top window 5000. Similarly window 5300 provides a touch command method of assigning color codes for selected medical disorders, which will be handy during the next stage of the analysis. The doctor can select a color code according to the number of medical disorders selected. A simple touch of each medical disorders number in window 5300 will provide the user with choice of all available colors and the user can select the desired color by the second touch. Alternatively, the user can change color by each single touch until the desired color is seen. Color code can be used by the user of the system to easily distinguish disorders. For example, mark more serious disorders with dark colors, while less sever disorders will be marked by light colors. In case of numerous medical records represented on a single chart such color differentiation of disorders into two or more categories provides simple and convenient initial visual analysis.

Figure 6:
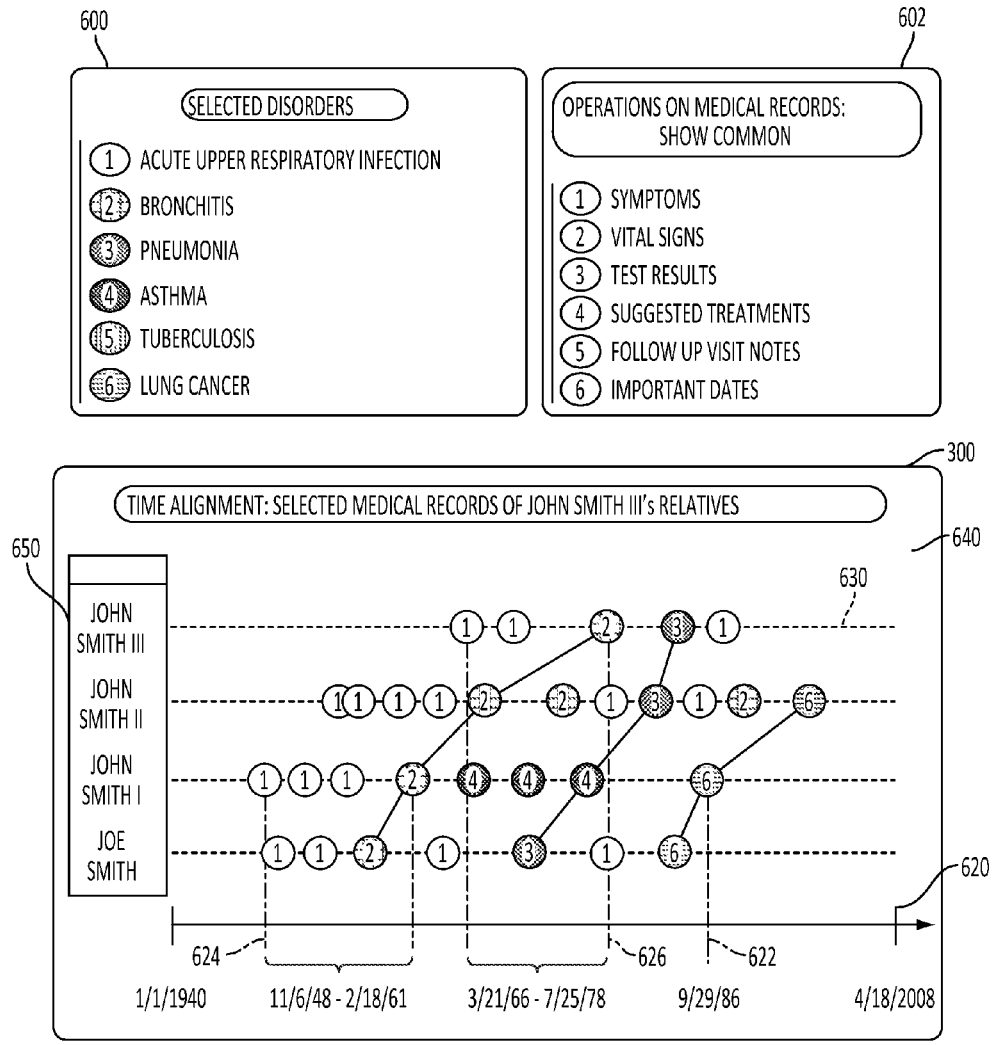
FIG. 6 illustrates a process of connecting medical disorders of selected family members for further comparison by a touch command according to one of the embodiments of the present application.

Once the process of combining selected medical disorders with selected family members is complete, two new windows 600 and 640 appear as seen in FIG. 6. Window 600 shows the list of selected medical disorders with the chosen color codes, and the window 640 has the charts of medical disorders aligned with the timeline for each of the selected family members. These charts are based on medical records invoked by the system for selected family members from the data base. The electronic medical records are built using a document format allowing easy interoperability. It should be noted, that many medical record formats exist. Any method of formatting medical records would suffice for the present invention as long as it is structured and consistent. Example of a simple XML based medical record is presented in FIG. 6B.

Another example could be the Health Level Seven (HL7) Clinical Document Architecture (CDA) Release 2.0 standard of EMR representation. The HL7 CDA is an XML-based markup standard intended to specify encoding, structure and semantics.

The physical medical records may be the property of the medical provider (or facility) that prepares them. This includes films and tracings from diagnostic imaging procedures such as X-ray, CT, PET, MRI, ultrasound, etc. The patient, however, according to HIPAA, would own the information contained within the record and has a right to view the originals, and to obtain copies under the current law. Therefore, the patient and patient's family members can provide all these records or the right to view the records to the doctor using the system. The invented system also has access to the profile of each patient whose medical records are available to the system. Information in the profile includes but is not limited to a unique patient ID, ID's of patients parent's, children, and siblings. Information is stored in structured format such as XML in a database. Example of such a profile is illustrated in FIG. 6C.

The system can therefore link patients with their medical records and their relatives and the corresponding medical records. As was shown in FIG. 1, the computing device on which the invented system is implemented is connected to the network through the network interface and therefore the system can easily retrieve desired records from remote database or other computers that provide authorized access to the medical records.

The value of this method comes in the easy and intuitive way of comparing related medical disorders of selected family members. If the doctor suspects some pattern in medical disorder developments among various family members, he can simply connect the circles representing relevant medical records with the diagnosis shown in the selected medical disorders list. For example in window 640, the doctor may want to compare the medical records when bronchitis was diagnosed to each of the family members. This is done by touch command where the doctor would place his finger, via touch screen 300, on the selected medical record and move it from there to the next one, etc., thus connecting them with a line. Once linking of records is completed, the doctor can invoke all the desired records and ask the system to show full records, or their common information, or the differences. For example, the doctor may want to see what symptoms were recorded for each person, and how symptoms for John Smith III differ from symptoms recorder for other family members when bronchitis was first diagnosed.

The doctor can also easily check the dates of each of the medical records shown in the chart by touching the circle representing a medical record and moving his finger all the way down to the timeline. This touch command is interpreted by the system as "SHOW DATE OF THE MEDICAL RECORD", and a dotted vertical line connecting the circle representing the medical record with the timeline and the corresponding timeline next to the vertical line are displayed in the chart. For example, in FIG. 6 the timing 622 of lung cancer for John Smith I is shown as Sep. 29, 1986.

Likewise by simultaneously touching two circles representing medical records with two fingers, the doctor can move both fingers down to the time line to see the time interval between the two events recorded in the touched medical records. For example, in FIG. 6, two such time intervals are illustrated for medical records of John Smith I (624) and John Smith III (626) connecting first occurrence of Acute Upper Respiratory Infection with the first occurrence of Bronchitis for each of the patients. The corresponding time intervals are Nov. 6, 1948-Feb. 18, 1961 and Mar. 21, 1966-Jul. 25, 1978, respectively.

Examples presented above illustrate advantages of the invented system. The doctor, or any other person examining medical records, can easily visualize timing of critical events related to the current medical disorder of the patient, and decide where to concentrate examiner's effort for further medical analysis. Few selected patients and selected medical disorders are combined by a touch command illustrated in FIG. 5. User's finger may perform, via touch screen 300, touching "Selected Disorders" button 5210 in window 5200 moving into the window 5000. As a result the system retrieves all relevant medical records as is illustrated in flow chard shown in FIG. 7 below, and constructs timeline of selected medical disorders for each selected patient as shown in FIG. 6. For example in windows 640, timeline 630 corresponds to recorded medical disorders for John Smith III, and includes three instances of acute upper respiratory infection (white colored circles), one instance of bronchitis diagnosis, and one instance pneumonia diagnosis. Medical records are retrieved from local or remote depositories with secure authorized access.

As shown in FIG. 6 the doctor has the flexibility of selecting more than one suspected pattern. For example, in addition to connecting medical records of first diagnosis of bronchitis, the doctor has also selected two other suspected patterns. One suspected pattern of lung cancer records, and a pattern of the latest most severe, but not terminal lung medical disorders: asthma for John Smith I and pneumonia for the others. In order to compare the linked records, the user would place his finger, via touch screen 300, on any element in the link and touch with his other finger the appropriate touch-button "Operations on Medical Records: SHOW COMMON" in window 602. For example, if he selects to SHOW COMMON Symptoms, the system will automatically scan the linked records and identify symptoms that are common in each medical records and which lead to the recorded diagnosis. That (as well as additional easily accessible) information could help the physician to better diagnose John Smith III. It should be noted that other operations on the records are possible. For example, SHOW ALL, or SHOW DIFFERENCES, etc. Alternatively, the user can use voice recognition system built into the computing platform, and instruct the system shown the linked records, or to performed above mentioned operations on the records and display the results.

Figure 5:
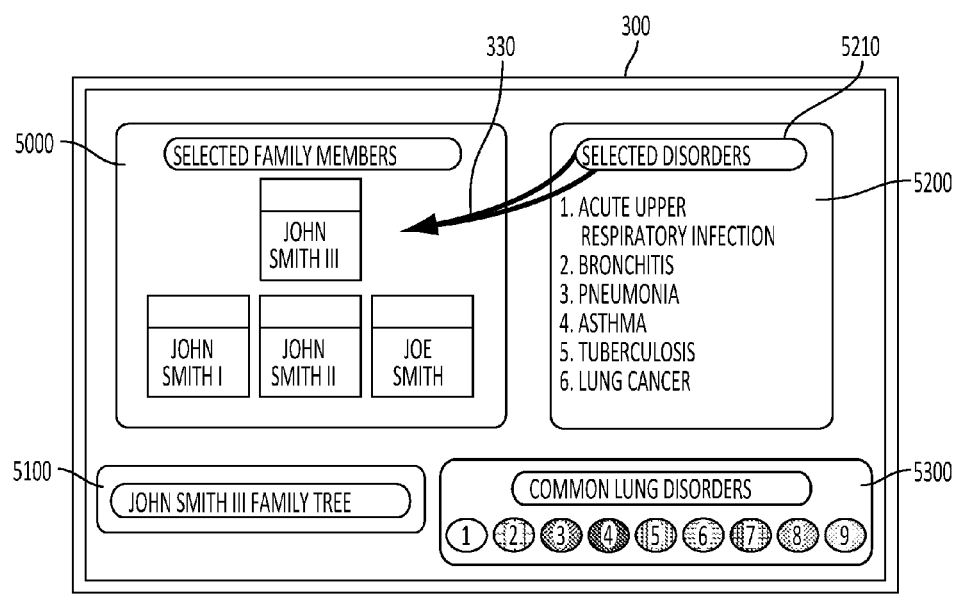
FIG. 5 illustrates a process of combining selected family members with the set of selected medical disorders by a touch command according to one of the embodiments of the present application.
Figure 7:
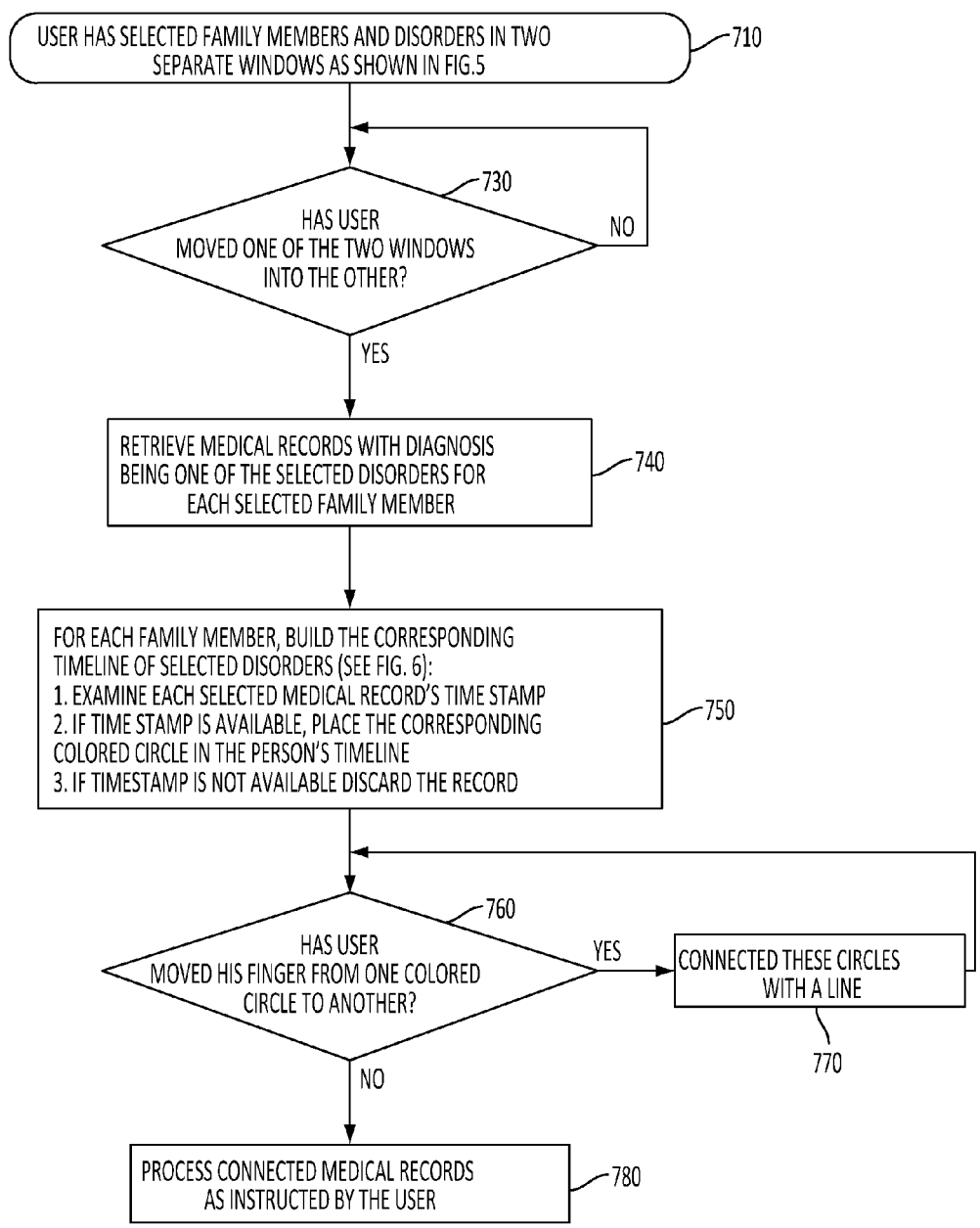
FIG. 7 illustrates a process of combining selected patients with a selected set of medical disorders and building timelines of the corresponding medical records according to one embodiment of the present application.

Flow chart illustrating the process of combining selected patients with the selected set of medical disorders and building timelines of the corresponding medical records is shown in FIG. 7. Referring to FIG. 7, step 710 corresponds to the process of the user (e.g., a physician) selecting family members of the patient (described earlier and illustrated in a flow chart in FIG. 3C) and medical disorders in two separate windows as was shown in FIG. 5. Step 730 corresponds to moving one of the two windows with selected family members and selected disorders into another. The process is illustrated in FIG. 5, and the implementation is very similar to the window movement shown in FIG. 3B and described in a flow chart seen in FIG. 3D. Step 740 corresponds to retrieval of medical records related to selected disorders of the selected family members and its example of its implementation is shown in the flow chart in FIG. 8.

Figure 8:
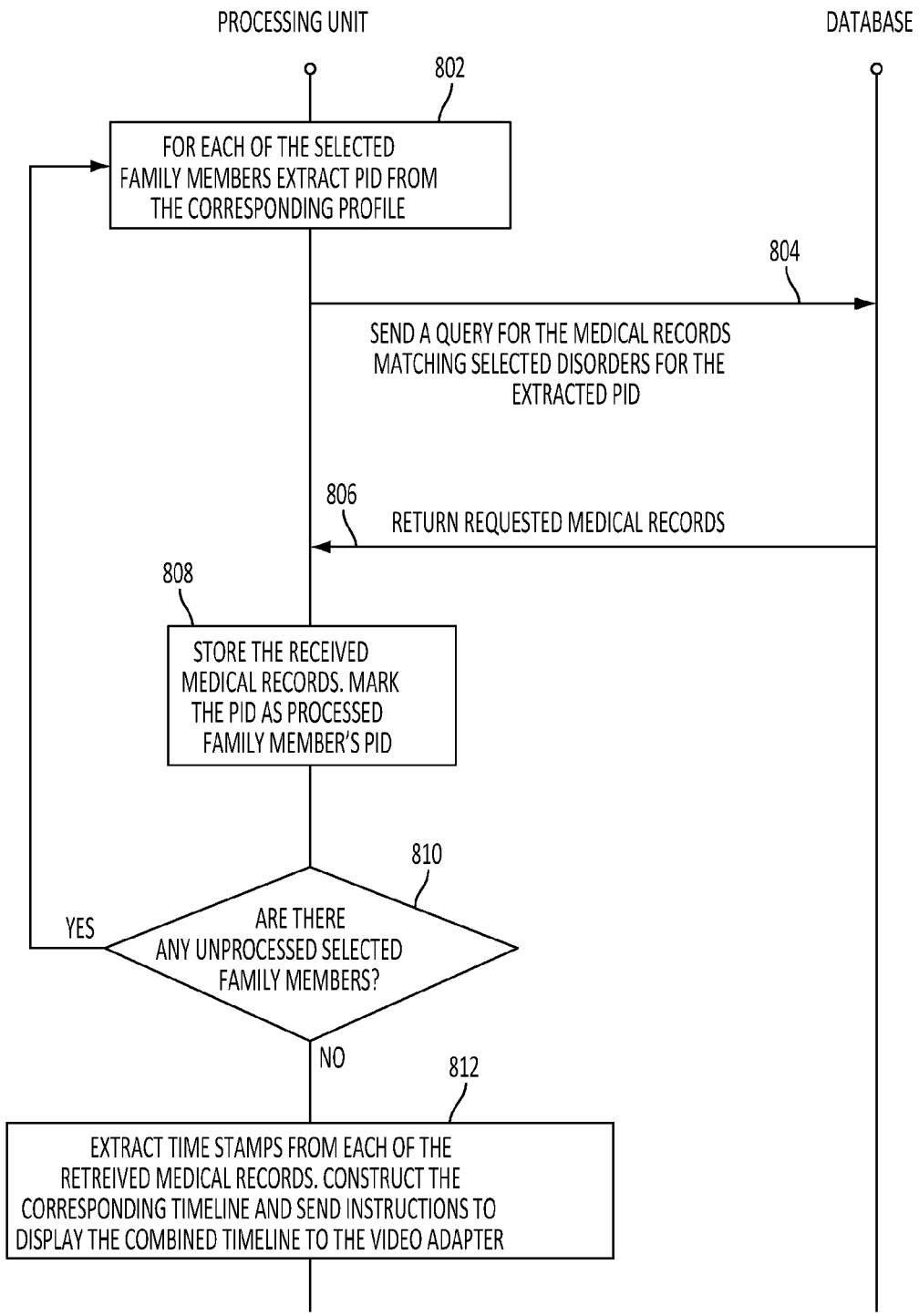
FIG. 8 illustrates a process of retrieval of medical records for the selected family members according to one embodiment of the present application.

Step 750 is done by the software running on the processing unit (see also the last step in the flow chart of FIG. 8). Steps 760 and 770 correspond to touch detections of circles corresponding to the medical events on the diagram 640 displayed on the touch screen and are implemented similar to one of the touch detections illustrated earlier and is based on message exchange between touch sensor and controller and the processing unit (see, for example, FIG. 3D). As was mentioned earlier, various touch sensing technologies can be used in the system. Preferred embodiment of the invention assumes acoustic based touch sensing technology. High level illustration of an acoustic based touch sensing technology is provided in FIG. 2. For more detailed illustration of how such system can be implemented please refer to one of the previous invention disclosure titled "Repetitive touch combining method".

FIG. 8 illustrates a process of retrieval of medical records for the selected family members according to one embodiment of the present application. At 802 and 804, based on patient ID (PID) shown as one of the fields in XML formatted patient's profile in FIG. 6C, the system forms an SQL query for the medical records related to selected disorders of the patient. Referring to FIG. 1, in the preferred embodiment, the request is sent by the processing unit 112 via the system bus 11, network interface 114 to the database 1141. At 806, requested medical records are returned by the database 1141. At 808, the received medical records are stored. At 810, it is checked whether there are any other unprocessed selected family members left. If yes, the process of retrieving the medical records for these unprocessed family members is repeated until there are no more unprocessed selected family members left. At 812, time stamps are extracted for each of the received medical records, a timeline is constructed for each family member and instructions to display the combined timelines are sent to the video adapter.

It should be noted that presented system and method and touch screen interface can be adapted to variety of applications where records of various events are being studied for possible patterns and compared with each other or some other information. For example, another embodiment is the system that provides access to quarterly (or annual) financial statements of companies in the same sector of the economy. In another embodiment, historical records of events of a certain type for similar countries is specified for periods of time that can be compared using a similar system. Similarly one can easily extend the described system and method for analysis of purchase orders, or other type of standardized records where repetitive patterns can be observed and analyzed by the users.

Those of skill in the art would understand that information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

Those of skill would further appreciate that the various illustrative logical blocks, modules, circuits, and algorithm steps described in connection with the disclosure herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the disclosure herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the disclosure herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary designs, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a general purpose or special purpose computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The previous description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein, but is to be accorded the widest scope consistent with the principles and novel features disclosed herein.

What is claimed is:

1. A method for analyzing data records using a touch screen interface, the method comprising:
    receiving a touch event from the touch screen interface;
    in response to receiving the touch event, selecting at least two data records from a plurality of data records in a time chart, the time chart including at least one time line relating to at least one data object, the plurality of data records being plotted on the at least one time line based on a time parameter of each of the plurality of data records;
    processing at least one information parameter relating to the selected at least two data records based on the time parameter, the at least one information parameter corresponding to a medical condition included in the at least two data records;
    displaying the at least one information parameter for both the at least two data records at corresponding positions on the time line to display time occurrences when the medical condition was identified for both the at least two data records; and
    creating a link between the at least two data records responsive to the touch event.

2. The method of claim 1, wherein the touch event comprises:
    simultaneously touching representations of the two data records on a touch sensitive screen of the touch screen interface using a touch input device;
    dragging the representations on to a time axis on the time chart.

3. The method of claim 2 wherein:
    processing the at least one information parameter comprises determining a time interval between the two selected data records based on the time parameter of each of the two data records.

4. The method of claim 1, wherein the touch event comprises:
    touching a first representation of a first data record from the time chart on a touch sensitive screen of the touch screen interface using a touch input device; and
    dragging the touch input device from the representation of the first data record to at least a second representation of a second data record.

5. The method of claim 1, further comprising:
    determining information common to the linked first and second data records.

6. The method of claim 1, wherein the touch event comprises:

touching a representation of the at least two data records from the time chart on a touch sensitive screen of the touch screen interface using a touch input device; and dragging the representation on to a time axis on the time chart.

7. The method of claim 6 wherein:

processing the information comprises determining a time of recordation of the at least two data records based on time parameters of the at least two data records.

8. An apparatus for analyzing data records using a touch screen interface, the apparatus comprising:

at least one processor configured to:

receive a touch event from the touch screen interface;

in response to receiving the touch event, select at least two data records from a plurality of data records in a time chart, the time chart including at least one time line relating to at least one data object, the plurality of data records being plotted on the at least one time line based on a time parameter of each of the plurality of data records;

process at least one information parameter relating to the selected at least two data records based on the time parameter, the at least one information parameter corresponding to a medical condition included in the at least two data records;

display the at least one information parameter for both the at least two data records at corresponding positions on the time line to display time occurrences when the medical condition was identified for both the at least two data records; and create a link between the at least two data records responsive to the touch event; and a memory coupled to the at least one processor.

9. The apparatus of claim 8, wherein the touch event comprises:

simultaneously touching representations of the two data records on a touch sensitive screen of the touch screen interface using a touch input device;

dragging the representations on to a time axis on the time chart.

10. The apparatus of claim 9 wherein:

the processor is configured to process the at least one information parameter by determining a time interval between the two selected data records based on the time parameter of each of the two data records.

11. The apparatus of claim 8, wherein the touch event comprises:

touching a first representation of a first data record from the time chart on a touch sensitive screen of the touch screen interface using a touch input device; and dragging the touch input device from the representation of the first data record to at least a second representation of a second data record.

12. The apparatus of claim 8, wherein the processor is further configured to:

determine information common to the linked first and second data records.

13. The apparatus of claim 8, wherein the touch event comprises:

touching a representation of the at least two data records from the time chart on a touch sensitive screen of the touch screen interface using a touch input device; and dragging the representation on to a time axis on the time chart.

14. The apparatus of claim 13 wherein:

the processor is configured to process the information by determining a time of recordation of the at least two data records based on time parameters of the at least two data records.

15. A non-transitory computer-program product configured to store instructions that when executed cause a processor to perform analyzing data records using a touch screen interface, the processor being further configured to perform:

receiving a touch event from the touch screen interface;

in response to receiving the touch event, selecting at least two data records from a plurality of data records in a time chart, the time chart including at least one time line relating to at least one data object, the plurality of data records being plotted on the at least one time line based on a time parameter of each of the plurality of data records;

processing at least one information parameter relating to the selected at least two data records based on the time parameter, the at least one information parameter corresponding to a medical condition included in the at least two data records;

displaying the at least one information parameter for both the at least two data records at corresponding positions on the time line to display time occurrences when the medical condition was identified for both the at least two data records; and creating a link between the at least two data records responsive to the touch event.

16. The non-transitory computer-program product of claim 15, wherein the touch event comprises:

simultaneously touching representations of the two data records on a touch sensitive screen of the touch screen interface using a touch input device;

dragging the representations on to a time axis on the time chart.

17. The non-transitory computer-program product of claim 16, wherein the processor is further configured to perform:

processing the at least one information parameter comprises determining a time interval between the two selected data records based on the time parameter of each of the two data records.

18. The non-transitory computer-program product of claim 15, wherein the touch event comprises:

touching a first representation of a first data record from the time chart on a touch sensitive screen of the touch screen interface using a touch input device; and dragging the touch input device from the representation of the first data record to at least a second representation of a second data record.

19. The non-transitory computer-program product of claim 15, wherein the processor is further configured to perform:

determining information common to the linked first and second data records.

20. The non-transitory computer-program product of claim 15, wherein the touch event comprises:

touching a representation of the at least two data records from the time chart on a touch sensitive screen of the touch screen interface using a touch input device; and dragging the representation on to a time axis on the time chart.

21. The non-transitory computer-program product of claim 20 wherein the processor is further configured to perform:

processing the information comprises determining a time of recordation of the at least two data records based on time parameters of the at least two data records.

* * * * *